US010642960B2

(12) United States Patent
Goguen

(10) Patent No.: US 10,642,960 B2
(45) Date of Patent: May 5, 2020

(54) WEARABLE KIT WITH SMART PATCH

(71) Applicant: KONINKLIJKE PHILIPS N.V., Eindhoven (NL)

(72) Inventor: Jonathan T. Goguen, Brookline, NH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 38 days.

(21) Appl. No.: 15/537,992

(22) PCT Filed: Dec. 17, 2015

(86) PCT No.: PCT/EP2015/080117
§ 371 (c)(1),
(2) Date: Jun. 20, 2017

(87) PCT Pub. No.: WO2016/102284
PCT Pub. Date: Jun. 30, 2016

(65) Prior Publication Data
US 2017/0351840 A1 Dec. 7, 2017

Related U.S. Application Data

(60) Provisional application No. 62/095,169, filed on Dec. 22, 2014.

(30) Foreign Application Priority Data

Jun. 11, 2015 (EP) .................................. 15171622

(51) Int. Cl.
*G06F 19/00* (2018.01)
*G16H 40/63* (2018.01)
*A61K 9/70* (2006.01)

(52) U.S. Cl.
CPC ........ *G06F 19/3462* (2013.01); *A61K 9/7023* (2013.01); *G16H 40/63* (2018.01)

(58) Field of Classification Search
None
See application file for complete search history.

(56) References Cited

U.S. PATENT DOCUMENTS

| 2007/0196456 | A1  | 8/2007 | Stevens et al. |
| 2008/0119707 | A1* | 5/2008 | Stafford ............... A61B 5/6833 600/365 |
| 2015/0217054 | A1* | 8/2015 | Booth .................. G06F 19/3468 604/504 |

FOREIGN PATENT DOCUMENTS

WO     2013142339 A1    9/2013

OTHER PUBLICATIONS

European Search Report for EP Application No. 15171622, dated Nov. 24, 2015.

* cited by examiner

*Primary Examiner* — Curtis A Kuntz
*Assistant Examiner* — Shawna M Kingston

(57) ABSTRACT

A system and method for controlling medication-dispensing patches by a wearable device is provided. The method comprises receiving a transmission at a wearable device, wherein the transmission identifies a medication-dispensing patch; transmitting information corresponding to the identified medication-dispensing patch to an external computing device; receiving information at the wearable device from the external computing device, wherein the received information corresponds to a dosage of a medication that should be dispensed by the medication-dispensing patch; and transmitting information from the wearable device, wherein the transmission is configured for controlling a medication dosage that is dispensed by the medication-dispensing patch.

13 Claims, 8 Drawing Sheets

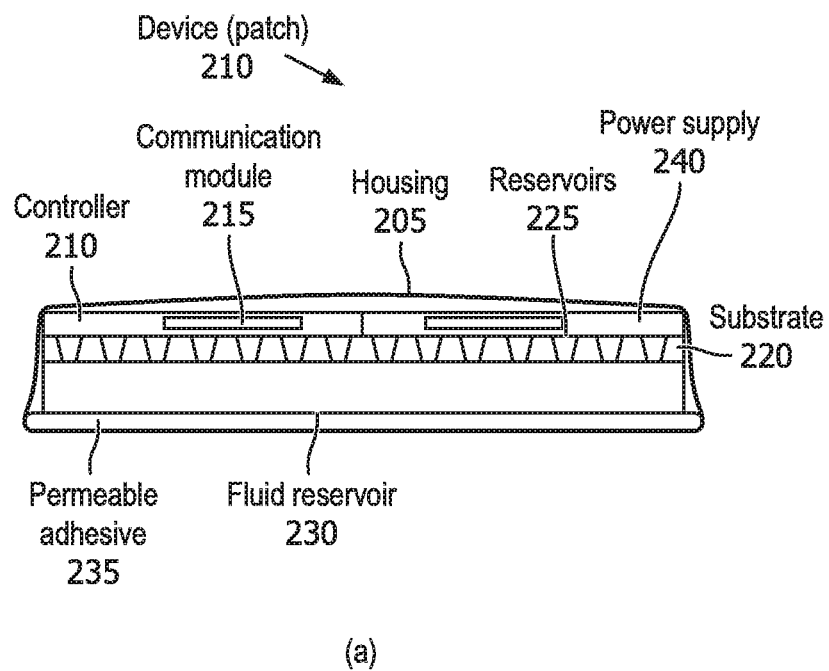
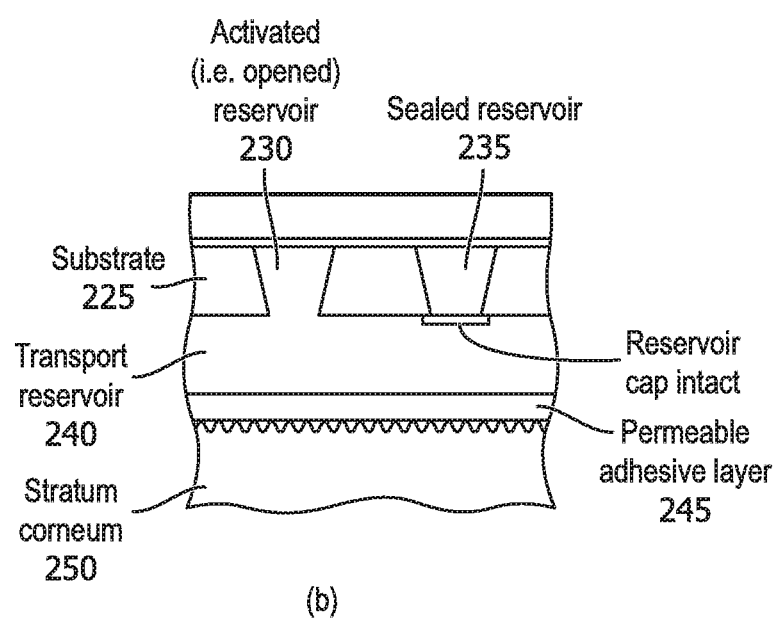
FIG. 2

Manufacturer portal database — 400
Patient ID: TNelson-7356 — 401

| Active ingredient | Patch ID | Dose timing | Doctor | Pharmacist | Wearable capabilities | Condition criteria | Condition duration | Condition action |
|---|---|---|---|---|---|---|---|---|
| Pacerone | 123ABC | 24 hrs. | Smith | Jones | Heart rate activity | <100 bpm; normal activity<br>100-130 bpm, normal activity<br>>130; normal activity<br>100-140; heavy activity | 6 hours<br>1 hour<br>10 min<br>30 min | Do nothing<br>Standard dose<br>Suppl. dose 20%<br>Standard dose |
| Lasix | 123ABC | 24 hrs. | McGann | Jones | Blood pressure | <90 sys<br>90-120 sys<br>>120 sys | 2 days<br>2 days<br>2 days | Nothing<br>Standard dose<br>Standard dose +5% |
| Belsomra | 789XYZ | 8PM-6AM | Freud | Singh | Sleep | Sleep cycle 1-2<br>Sleep cycle 3-4<br>Sleep cycle 5+ | N/A | Standard dose<br>Reduce dose 75%<br>Nothing |
| Nicotine | NIC157 | 8AM-8PM | N/A | OTC | Meals | No alcohol, under 1000 cal<br>No alcohol, over 1000 cal<br>Alcohol, any calories | N/A | Do nothing<br>Delay dosage 20 min.<br>Delay dosage 2 hours |
| Vitamin B-12 | B12-001 | 8AM-8PM | N/A | OTC | Mood | Trending negative<br>Trending positive | 2 hours<br>2 hours | Standard dose<br>No dose |

FIG. 4

500 — Patch program
501 — Patch ID: 123ABC

| Active ingredient | Dose timeline | Std. dose reservoirs | Wearable capabilities | Condition criteria | Condition duration | Reservoir release interval (minutes) |
|---|---|---|---|---|---|---|
| Pacerone | 24 hrs | 10 | Heart rate, activity | <100 bpm | 6 hours | 0 |
| | | | | 100-130 bpm; normal activity | 1 hour | 144 |
| | | | | >130; normal activity | 10 min | 120 |
| | | | | 100-140; heavy activity | 30 min | 144 |
| Lasix | 24 hrs | 20 | Blood pressure | <90 sys | 2 days | 0 |
| | | | | 90-120 sys | 2 days | 72 |
| | | | | >120 sys | 2 days | 66 |

505 — Active ingredient
515 — Std. dose reservoirs
520 — Wearable capabilities
525 — Condition criteria
530 — Condition duration
535 — Reservoir release interval (minutes)
510 — Dose timeline
540 — Pacerone row
545 — Lasix row (a)

550 — Patch data
551 — Patch ID: 123ABC

| Active ingredient | Reservoir numbers | # reservoirs consumed |
|---|---|---|
| Pacerone | 1-100 | 60 |
| Lasix | 101-200 | 135 |

555 — Active ingredient
560 — Reservoir numbers
565 — # reservoirs consumed
570 — Pacerone row
575 — Lasix row (b)

FIG. 5

WEARABLE KIT WITH SMART PATCH

CROSS-REFERENCE TO PRIOR APPLICATIONS

This application is the U.S. National Phase application under 35 U.S.C. § 371 of International Application No. PCT/EP2015/080117, filed on Dec. 17, 2015, which claims the benefit of European Application No. 15171622.2, filed Jun. 11, 2015 and of U.S. Provisional Application Ser. No. 62/095,169, filed Dec. 22, 2014. These applications are hereby incorporated by reference herein, for all purposes.

BACKGROUND

Technical Field

The present invention generally relates to a medicine-dispensing smart patch, and more specifically to a smart patch that dispenses medication to a patient according to information transmitted to the smart patch from a wearable device.

Description of the Related Art

Wearable electronic devices, or as used herein, wearable technology is a new class of electronic systems that can provide data acquisition through a variety of unobtrusive sensors that may be worn by a user. The sensors gather information, for example, about the environment, the user's activity, or the user's health status. However, there are significant challenges related to the coordination, computation, communication, privacy, security, and presentation of the collected data. Additionally, there are challenges related to power management given the current state of battery technology. Furthermore, analysis of the data is needed to make the data gathered by the sensors useful and relevant to end-users. In some cases, additional sources of information may be used to supplement the data gathered by the sensors. The many challenges that wearable technology presents require new designs in hardware and software.

Wearable technology includes mobile electronic devices that can be worn on the body, or attached to or embedded in clothes and accessories of an individual. The designs of wearable technology often incorporate practical functions and features, but may also have a critical or aesthetic agenda. Processors and sensors associated with the wearable technology can gather, process, and display information to a user. Wearable technology may be utilized in a variety of areas including monitoring health of a user and providing other types of data and statistics. Examples of wearable technology in the health arena include the FitBit, the Nike FuelBand, and the Apple Watch.

Wearable devices currently do not communicate with medicine-dispensing smart patches where the smart patches may dispense medications to a patient according to information transmitted to the smart patch from a wearable device.

SUMMARY

A first aspect of the invention includes a computer-implemented method for dispensing a medication at a transdermal patch. The method comprises receiving a transmission at a wearable device, wherein the transmission identifies a medication-dispensing patch; transmitting information corresponding to the identified medication-dispensing patch to an external computing device; receiving information at the wearable device from the external computing device, wherein the received information corresponds to a dosage of a medication that should be dispensed by the medication-dispensing patch; and transmitting information from the wearable device, wherein the transmission is configured for controlling a medication dosage that is dispensed by the medication-dispensing patch.

A second aspect of the invention includes a non-transitory computer readable storage medium having embodied thereon a program executable by a processor to perform a method for dispensing a medication at a transdermal patch. The method comprises receiving a transmission over a communications module at a wearable device, wherein the transmission is configured for identifying a medication-dispensing patch; transmitting the information corresponding to the identified medication-dispensing patch to an external computing device using the communications module; receiving information at the wearable device from the external computing device using the communications module, wherein the received information corresponds to a dosage of a medication that should be dispensed by the medication-dispensing patch; and transmitting information from the wearable device using the communications module, wherein the transmission is configured for controlling a medication dosage that is dispensed by the medication-dispensing patch.

A third aspect of the invention provides a system for dispensing a medication at a transdermal patch. The system comprises a medication-dispensing patch configured for communicating over a wireless communication network; an external computing device configured for communicating over the wireless communication network; and a wearable device configured for receiving a transmission for identifying the medication-dispensing patch; transmitting the received information to the external computing device; receiving information from the external computing device regarding a dosage of a medication that should be dispensed by the medication-dispensing patch; and transmitting instructions to the medication-dispensing patch, wherein the medication-dispensing patch is configured for controlling a medication dosage that is dispensed in accordance with the instructions.

The current invention aims to provide improved systems and methods that coordinate the delivery of transdermal medications according to information transmitted to a smart patch.

BRIEF DESCRIPTION OF THE DRAWINGS

FIG. 2A illustrates a cross sectional drawing of a drug delivery patch that administers a drug through the skin according to an embodiment of the present invention.

FIG. 2B illustrates a semi-cross sectional view of smart drug delivery patch according to an embodiment of the present invention.

FIG. 4 illustrates a manufacturer portal database that contains information regarding medicines in a smart patch and other related information according to an embodiment of the present invention.

FIG. 5A illustrates information that a patch program may monitor, and adjustments that the patch program may initiate according to the monitored information according to an embodiment of the present invention.

FIG. 5B illustrates patch data information that identifies various parameters of different smart patches according to an embodiment of the present invention.

DETAILED DESCRIPTION

Embodiments of the present invention generally relate to systems and methods for controlling medication-dispensing patches by a wearable device. A wearable device after receiving information relating to a medication-dispensing patch and dosage instructions from a doctor may transmit instructions to the medication-dispensing patch that control how much medication should be released by the patch.

Wearable devices and mobile electronic devices described herein may communicate using any data communication technology known, including, but not limited to cellular 3G-4G LTE, Wi-Fi (802.11), near field data communications, and Bluetooth. In certain instances, a wearable device may include a plurality of data communication interfaces, a processor, a memory, a field programmable gate array (FPGA), an application specific integrated circuit (ASIC).

Medicinal dispensing patches may also communicate using any known data communication technology. A medicinal dispensing patch may include a processor, a memory, a micro-controller, a field programmable gate array (FPGA), an application specific integrated circuit (ASIC), and/or a state machine.

Mobile electronic devices described herein include, but are not limited to smartphones, iPhones, Android phones, iPads, and notebook computers. Communications by a wearable device or by a mobile device may be communicated over any data communication technology known in the art, including, but not limited to Bluetooth, Cellular 3G 4G LTE, and Wi-Fi (802.11). In certain instances, a mobile device may include a plurality of data communication interfaces, a processor, a memory, a field programmable gate array (FPGA), and an application specific integrated circuit (ASIC).

The various methods may be performed by software operating in conjunction with hardware. For example, instructions executed by a processor may otherwise be stored in a non-transitory computer readable medium such as memory. Various interfaces may be implemented—both communications and API. One skilled in the art will appreciate the various requisite components of a mobile device and integration of the same with one or more of the figures and/or descriptions included herein.

Figure 1:
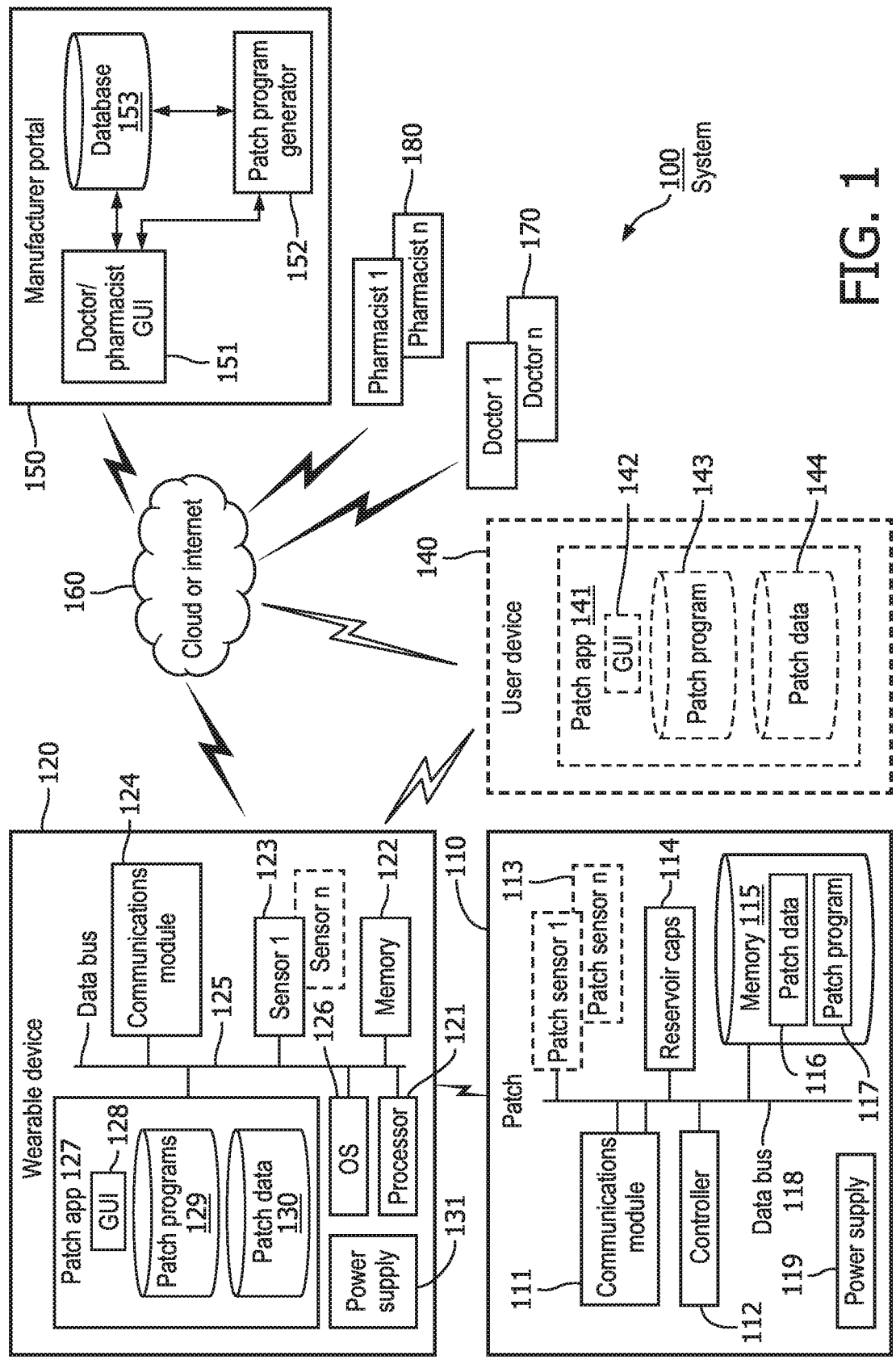
FIG. 1 illustrates an exemplary drug delivery patch consistent with the disclosure of the present invention.

FIG. 1 illustrates an exemplary system with a drug delivery patch consistent with the disclosure of the present invention. The wearable kit with smart patch system 100 of FIG. 1 includes a user device 140, a wearable device 120, pharmacists 1 through N 170, doctors 1 through N 180, a manufacturer portal 150 communicating over a network communication interface through the cloud or internet 160. The wearable device 120 in FIG. 1 communicates with a drug delivery patch 110 over a data communication module 124.

The drug delivery patch 110 depicted includes a communications module 111, a controller 112, patch sensors 1-$n$ 113, a reservoir cap 114, and a memory 115 communicating over a communication bus 118. The drug delivery patch 110 also includes a power supply 119. The memory includes patch data 116 and a patch program 117.

The wearable device in FIG. 1 includes a processor 121, a memory 122, sensors 1-$n$ 123, and a communications module 124 communicating over a data bus 125. The figure also includes operating system software (OS) 126, and a patch application 127. The patch application 127 includes a graphical user interface (GUI) 128, patch programs 129, and patch data 130. The wearable device 130 also includes a power supply 131.

The user device 140 in FIG. 1 includes patch application (APP) software 141, a GUI 142, a patch program 143, and patch data 144. The manufacturing portal 150 in FIG. 1 includes a doctor/pharmacist GUI 151, a patch program generator 152, and a database 153. The wearable device 120 in FIG. 1 may directly or indirectly control when and how much medication is dispensed by the drug delivery patch 110. When the wearable device 120 directly controls the dispensing of medication at the wearable device, a transmission from the wearable device 120 to the patch 110 may instruct the patch 110 to dispense medication. In certain instances, the power supply 119 in the patch 110 supplies the energy to dispense the medication. In yet other instances, energy from the transmission that instructs the patch 110 to dispense the medication may be used to power the patch 110. In the instance where the received transmission is used to power the patch, the drug delivery patch may not dispense medication when it has not received a transmission. Energy received by the patch may be received over a coil of wire or coiled trace at a medicine-dispensing patch, and the energy may be harvested in a manner similar to how a radio frequency identifier (RFID) harvests energy from a transmission.

Embodiments of the present invention are not limited to a passive drug delivery patch, as the patch 110 may also administer a dosage of the medication according to a schedule or criteria received from the wearable device 120. Communications received by the wearable device 120 from a user mobile device 140, from doctors 1 through N 180 using a doctor mobile device, pharmacists 1 though N 170 using a pharmacist mobile device, from a manufacturing portal 150, or from a third party may be used to set or modify the administration of the drug by the patch 110.

FIG. 2A illustrates a cross sectional drawing of a drug delivery patch that administers a drug through the skin. The drug delivery patch 210 of FIG. 2A includes a patch housing 205, a micro-controller 210, a data communications module 215, a substrate 220, reservoirs 225, a fluid reservoir 230, a permeable adhesive 235, and a power supply 240.

FIG. 2B illustrates a semi-cross sectional view of a smart drug delivery patch. The patch of FIG. 2B includes a substrate 225, a reservoir with an open port 230, a reservoir with an sealed/intact port 235, a transport reservoir 240, a permeable adhesive layer 245 in contact with stratum corneum 250 layer of skin. The stratum corneum 250 is an epidermal layer of skin. The controller 210 may cause a reservoir in the patch 230 to open when a dosage of medicine should be dispensed. Once the reservoir in the patch 230 opens, the medicine flows to the transport reservoir 240, and then the medicine flows through the adhesive layer 245 to the skin 250 (e.g., stratum corneum) of a patient. The controller 210 may also open a reservoir in the patch 230 according to criteria received from a wearable device or may open one or more reservoirs when a transmission is received from a wearable device.

Figure 3:
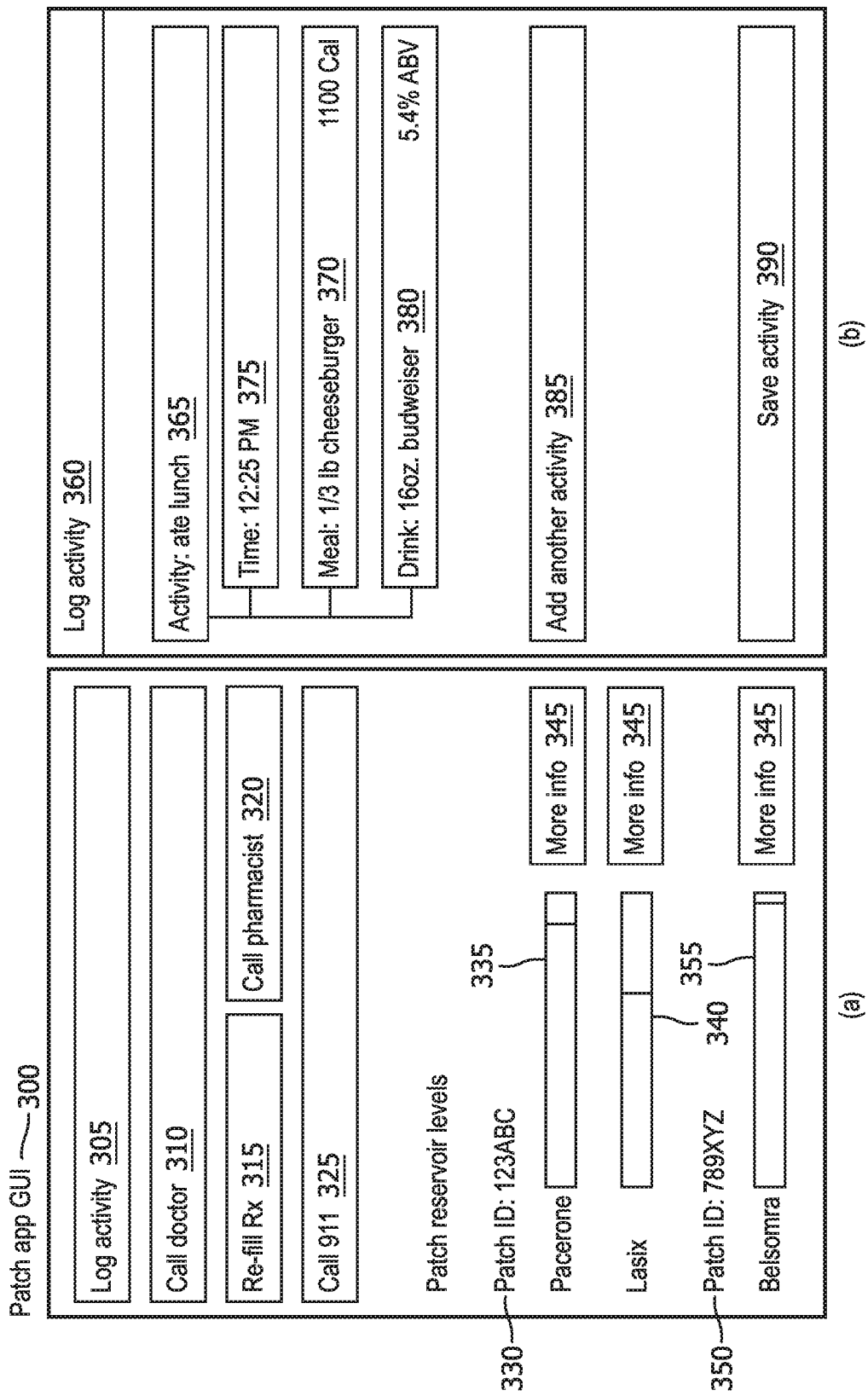
FIG. 3A illustrates a patch application graphical user interface (GUIs) according to an embodiment of the present invention.
FIG. 3B illustrates entries of activities that may be logged in an activity log according to an embodiment of the present invention.

FIG. 3A illustrates a patch application graphical user interface (GUI). FIG. 3A includes data entry boxes, selection boxes, and display fields. FIG. 3A includes a log activity selection box 305, a call doctor selection box 310, a refill prescription (Rx) selection box 315, a call pharmacist selection box 320, and a call 911 selection box 325. When one of these selection boxes is selected in a patch application (APP) GUI 300 of a mobile device or at a wearable device an appropriate action will be performed. For example, when the call doctor selection box 310 is selected the mobile device will call a doctor's office. Similarly, 911 325 or a pharmacist 320 may be called when a corresponding selection box is selected. In certain instances, a transmission from a wearable device may cause a user mobile device to make a call to a doctor, call 911, or call a pharmacist. When the refill RX selection box is selected 315, a user of the mobile device may be directed to a GUI where the user may enter prescription refill information. When the log activity selection box 305 is selected a log activity GUI 360 depicted in FIG. 3B may be opened.

The GUI of FIG. 3A also includes patch identifiers (ID) 330/350. Patch ID 123ABC 330 corresponds to a patch that contains the medications Pacerone 335 and Lasix 340. Bar graphs next to each identified medication provides an indication of how much Pacerone 335 and Lasix 340 medications remain in smart patch 123ABC 330. Similarly, patch ID 789XYZ 350 contains the medication Belsomra 355 and a bar graph next to the medication name provides an indication of how much Belsomra 335 remains in the patch. More information (info) selection boxes 345 next to each bar graph when selected may open another GUI that may provide additional information relating to the medication or to the patch. The patch application GUI 300 may be used to track and display information relating to amount, type, and other characteristics of medication(s) remaining in a medication-dispensing patch. This information may be used to inform a user of the wearable device that the medication-dispensing patch should be replaced when a medication runs low.

FIG. 3B illustrates entries of activities that may be logged in an activity log. An activity in the log activity GUI 360 includes information indicating that a patient ate a ⅓ pound (lb) cheeseburger 370 containing 1100 calories, the patient ate at 12:25 pm 375, and the patient drank 16 ounces of Budweiser beer 380 with an alcohol content of 5.4%. FIG. 3B also includes a selection box that when selected allows a user to enter another activity 385, and includes a save activity selection box 390 that allows the user to save data relating to an activity. The log activity GUI 360 may be used to monitor any type of activity that a user of a wearable device does. In certain instances, the log activity GUI 360 may also include information relating to an activity sensed by one or more sensors.

FIG. 4 illustrates a manufacturer portal database that contains information regarding medicines in a smart patch and other related information. Column headers in a table in the manufacturing portal data base 400 include active ingredient 405, patch identifier (ID) 410, dose timing 415, doctor 420, pharmacist 425, wearable capabilities 430, condition criteria 440, condition duration 445, and condition action 450. The table of FIG. 4 cross-references a medication type by active ingredient to a patch ID 401, a frequency of dose timing, a prescribing doctor, a pharmacist, and actions monitored by a wearable device a period of time. This table also maintains a record of information that includes heart rate, blood pressure, sleep state, meal data, and mood. The table of FIG. 4 also tracks whether the administration of an active ingredient has been changed based on data sensed by the wearable device. The dose timing may include any one of a number of settings, such as administer over a 24 hour period or administer between 8 pm and 6 am only. The dose amount may also be varied according to condition criteria data and condition actions listed in the table.

For example, the bottom row 475 of the table of FIG. 4 indicates that vitamin B-12 was administered using patch ID B12-001 from 8 am to 8 pm in a day. This row of the table also identifies a pharmacist of OTC, that a wearable device was monitoring the mood of a patient. When the mood of the patient was trending negative, the patient was administered a standard dose of vitamin B12 for a period of 2 hours. Later when the wearable device determined that the patient mood was trending positive, no dose of vitamin B12 was dispensed for a period of 2 hours.

The first row 455 of FIG. 4 cross-references information when administering the medication Pacerone to control irregular heartbeat (tachycardia) of a patient. While the wearable device monitors heartbeat rate and a patient activity level, the administration of the drug Pacerone is varied according to heart rate and patient activity level. For first condition criteria where the patient heartbeat is less than 100 (<) BPM and the patient activity level was normal, no medication was administered over a 6 hour period. When a heartbeat of 100-130 BPM was measured over a period of an hour and the patient activity was normal, the patient was administered a standard dosage of Pacerone. Later when the patient heart rate exceeded 130 (>130) BPM and the patient activity was normal, the patient was administered an additional dosage of Pacerone. The elevated heart rate lasted 10 minutes after the additional dosage was administered. Then when a heart rate of 100-140 BPM was measured when the patient was performing heavy activity, the standard dose of Pacerone was administered during an exercise period of 30 minutes. In this instance activity level may be sensed by a sensor that measures the motions of the patient. A number of steps may be monitored, for example. The wearable device may communicate with the smart patch dispensing the Pacerone over a data communication interface and control how much medication is dispensed over time based on physiological measurements made by the wearable device. Similarly, the manufacturing portal database 400 cross-references parameters relating to the administration of different active ingredients using different smart patches. The second row 460 relates to the administration of Lasix, the third 465 row relates to the administration of Belsomra, and the fourth row 470 relates to the administration of Nicotine. Manufacturing portal 150 may transmit information or criteria to the wearable device when modifying software running on the wearable device 120 or when modifying information or criteria regarding how much and when a medication should or should not be dispensed.

FIG. 5A illustrates information that a patch program may monitor, and adjustments that the patch program may initiate according to the monitored information. The patch program table 500 in FIG. 5A includes column headers of active ingredient 505, dose timeline 510, standard (Std.) dose reservoirs 515, wearable capabilities 520, condition criteria 525, condition duration 530, and internal release interval 535 (in minutes). The patch program table 500 in FIG. 5A includes a first row 540 that identifies conditions for dispensing the medication Pacerone, and a second row 545 that identifies conditions for dispensing the medication Lasix. Medications Pacerone and Lasix are included in a smart patch with a patch ID of 123ABC 501. The second row 545 in FIG. 5A illustrates the medication Lasix being administered over a period of 24 hours. Information in this row indicates that smart patch 123ABC has 20 standard dosage reservoirs, and that a wearable device is monitoring blood pressure. The second row 545 of FIG. 5A includes three different sets of condition criteria that correspond to a reservoir release interval in minutes. When a patient measured systolic BP was <90 over a 2 day period, the reservoir release interval was 0 minutes (i.e., Lasix was not administered). When the patients measured BP was >90 over a 2 day period, the reservoir release interval was every 72 minutes. When the patient BP was >120 over a 2 day period, the reservoir release interval was every 66 minutes. Since each reservoir contains a known milligram dosage of medication, releasing a reservoir more frequently increases the dosage of medication provided to the patient over time. A dosage of medication may be released according to the set of condition criteria 525 that is cross-referenced with sensor data. In certain instances, sensor data sensed by a sensor at a medicine-dispensing patch may be cross-referenced with sensor data sensed by a sensor at a wearable device when determining whether or when to dispense a medication. For example, when a sensor at the medicine-dispensing patch detects a high heart rate or a muscle twitch, that data may be cross-referenced with step data sensed at the wearable device. When the step data sensed at the wearable device indicates that a user of the wearable device is exercising and when a sensor at the medicine-dispensing patch indicates that the user has a high heart rate or an excessive muscle twitch, the wearable device may instruct the medicine-dispensing patch not to dispense medication. As such, the wearable device may override or change criteria using information sensed by multiple sensors based on another set of criteria (e.g., since a high heart rate is expected when a person exercises, do not medicate).

FIG. 5B illustrates patch data information that identifies various parameters of a smart patch. FIG. 5B illustrates patch ID 123ABC 551 with an active ingredient of Pacerone, that has 100 reservoirs numbered 1-100, and where 1-60 reservoirs have been consumed. The patch data 550 of FIG. 5B also identifies that patch ID 123ABC 551 includes the active ingredient Lasix, has reservoir numbers 101-200, and that 101-135 reservoirs have been consumed.

Figure 6:
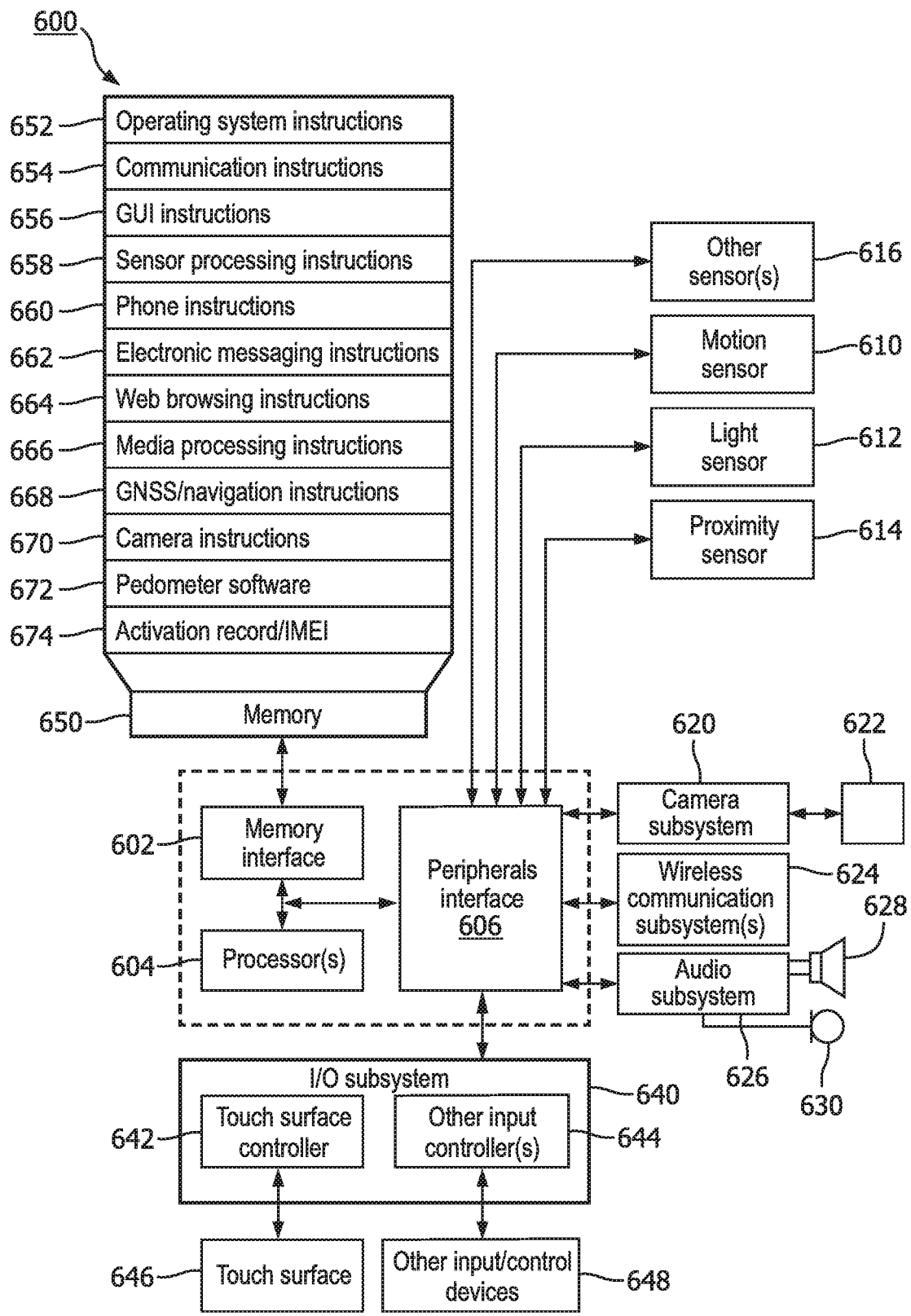
FIG. 6 illustrates a mobile device architecture that may be utilized to implement the various features and processes described herein according to an embodiment of the present invention.

FIG. 6 illustrates a mobile device architecture that may be utilized to implement the various features and processes described herein. Architecture 600 can be implemented in any number of portable devices including but not limited to smart wearable devices. Architecture 600 as illustrated in FIG. 6 includes memory interface 602, processors 604, and peripheral interface 606. Memory interface 602, processors 604 and peripherals interface 606 can be separate components or can be integrated as a part of one or more integrated circuits. The various components can be coupled by one or more communication buses or signal lines.

Processors 604 as illustrated in FIG. 6 are meant to be inclusive of data processors, image processors, central processing units, or any variety of multi-core processing devices. Any variety of sensors, external devices, and external subsystems can be coupled to peripherals interface 606 to facilitate any number of functionalities within the architecture 600 of the exemplar mobile device. For example, motion sensor 610, light sensor 612, and proximity sensor 614 can be coupled to peripherals interface 606 to facilitate orientation, lighting, and proximity functions of the mobile device. For example, light sensor 612 could be utilized to facilitate adjusting the brightness of touch surface 646. Motion sensor 610, which could be exemplified in the context of an accelerometer or gyroscope, could be utilized to detect movement and orientation of the mobile device. Display objects or media could then be presented according to a detected orientation (e.g., portrait or landscape).

Other sensors could be coupled to peripherals interface 606, such as a temperature sensor, a biometric sensor, or other sensing device to facilitate corresponding functionalities. Location processor 615 (e.g., a global positioning transceiver) can be coupled to peripherals interface 606 to allow for generation of geo-location data thereby facilitating geo-positioning. An electronic magnetometer 616 such as an integrated circuit could be connected to peripherals interface 606 to provide data related to the direction of true magnetic North whereby the mobile device could enjoy compass or directional functionality. Camera subsystem 620 and an optical sensor 622 such as a charged coupled device (CCD) or a complementary metal-oxide semiconductor (CMOS) optical sensor can facilitate camera functions such as recording photographs and video clips.

Communication functionality can be facilitated through one or more communication subsystems 624, which may include one or more wireless communication subsystems. Wireless communication subsystems 624 can include 802.x or Bluetooth transceivers as well as optical transceivers such as infrared. Wired communication subsystems can include a port device such as a Universal Serial Bus (USB) port or some other wired port connection that can be used to establish a wired coupling to other computing devices such as network access devices, personal computers, printers, displays, or other processing devices capable of receiving or transmitting data. The specific design and implementation of communication subsystem 624 may depend on the communication network or medium over which the device is intended to operate. For example, a device may include wireless communication subsystem designed to operate over a global system for mobile communications (GSM) network, a GPRS network, an enhanced data GSM environment (EDGE) network, 802.x communication networks, code division multiple access (CDMA) networks, or Bluetooth networks. Communication subsystem 624 may include hosting protocols such that the device may be configured as a base station for other wireless devices. Communication subsystems can also allow the device to synchronize with a host device using one or more protocols such as TCP/IP, HTTP, or UDP.

Audio subsystem 626 can be coupled to a speaker 628 and one or more microphones 630 to facilitate voice-enabled functions. These functions might include voice recognition, voice replication, or digital recording. Audio subsystem 626 in conjunction may also encompass traditional telephony functions.

I/O subsystem 640 may include touch controller 642 and/or other input controller(s) 644. Touch controller 642 can be coupled to a touch surface 646. Touch surface 646 and touch controller 642 may detect contact and movement or break thereof using any of a number of touch sensitivity technologies, including but not limited to capacitive, resistive, infrared, or surface acoustic wave technologies. Other proximity sensor arrays or elements for determining one or more points of contact with touch surface 646 may likewise be utilized. In one implementation, touch surface 646 can display virtual or soft buttons and a virtual keyboard, which can be used as an input/output device by the user.

Other input controllers 644 can be coupled to other input/control devices 648 such as one or more buttons, rocker switches, thumb-wheels, infrared ports, USB ports, and/or a pointer device such as a stylus. The one or more buttons (not shown) can include an up/down button for volume control of speaker 628 and/or microphone 630. In some implementations, device 600 can include the functionality of an audio and/or video playback or recording device and may include a pin connector for tethering to other devices.

Memory interface 602 can be coupled to memory 650. Memory 650 can include high-speed random access memory or non-volatile memory such as magnetic disk storage devices, optical storage devices, or flash memory. Memory 650 can store operating system 652, such as Darwin, RTXC, LINUX, UNIX, OS X, ANDROID, WINDOWS, or an embedded operating system such as VXWorks. Operating system 652 may include instructions for handling basic system services and for performing hardware dependent tasks. In some implementations, operating system 652 can include a kernel.

Memory 650 may also store communication instructions 654 to facilitate communicating with other mobile computing devices or servers. Communication instructions 654 can also be used to select an operational mode or communication medium for use by the device based on a geographic location, which could be obtained by the GPS/Navigation instructions 668. Memory 650 may include graphical user interface instructions 656 to facilitate graphic user interface processing such as the generation of an interface; sensor processing instructions 658 to facilitate sensor-related processing and functions; phone instructions 660 to facilitate phone-related processes and functions; electronic messaging instructions 662 to facilitate electronic-messaging related processes and functions; web browsing instructions 664 to facilitate web browsing-related processes and functions; media processing instructions 666 to facilitate media processing-related processes and functions; GPS/Navigation instructions 668 to facilitate GPS and navigation-related processes, camera instructions 670 to facilitate camera-related processes and functions; and instructions 672 for any other application that may be operating on or in conjunction with the mobile computing device. Memory 650 may also store other software instructions for facilitating other processes, features and applications, such as applications related to navigation, social networking, location-based services or map displays.

Figure 7:
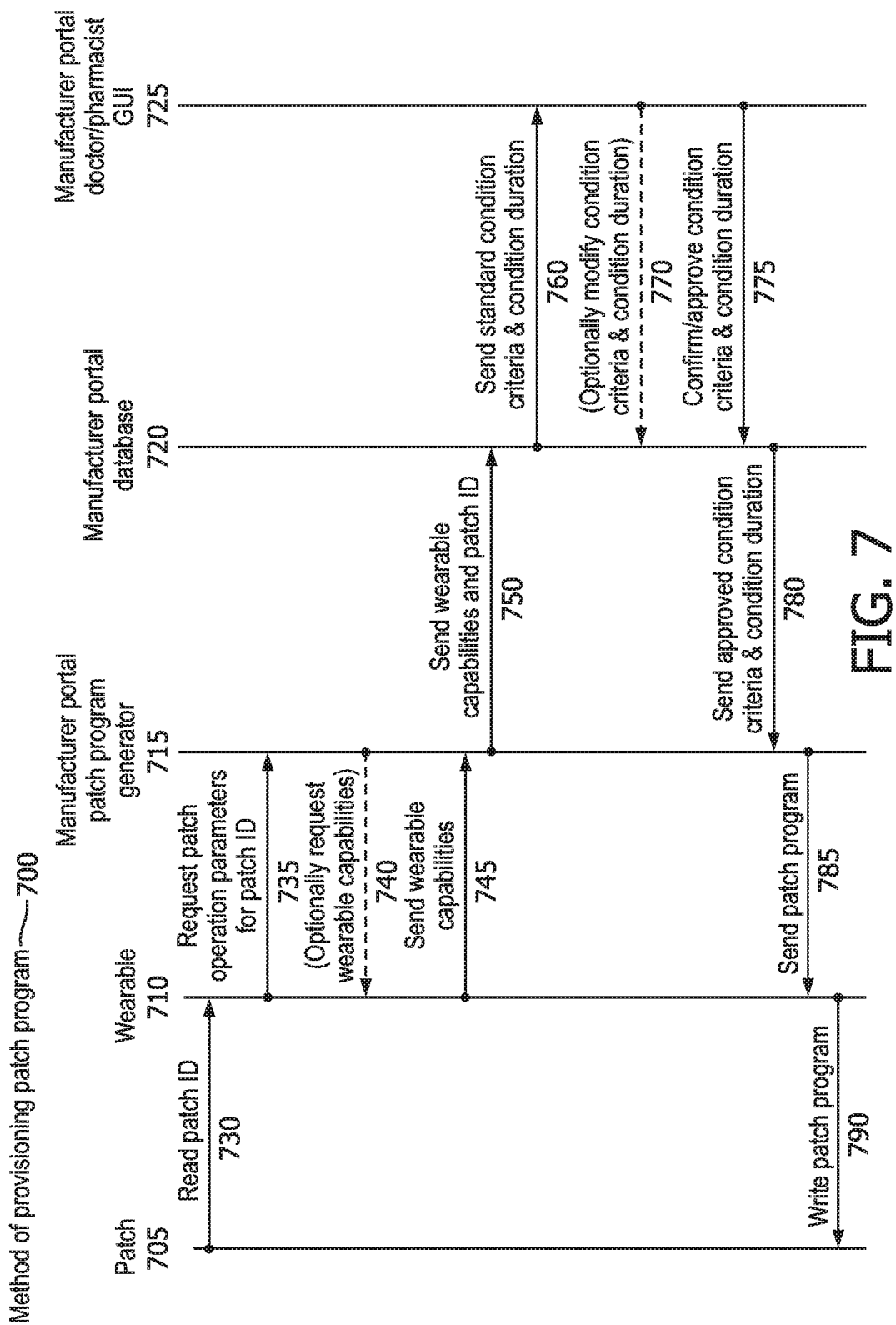
FIG. 7 illustrates a second methodology consistent with the disclosure of the present invention according to an embodiment of the present invention.

FIG. 7 illustrates a second methodology consistent with the disclosure of the present invention. The method for providing a patch program 700 begins by a wearable device 710 reading a patch ID 730 of a smart patch 705. The wearable device then transmits a communication 735 to a manufacturer portal patch program generator 715, and then the wearable device may optionally receive a request 740 from the manufacturing portal patch program generator 715. In response to the request the wearable device 710 may transmit information to the manufacturer portal patch program generator 715 that identifies capabilities 745 of the wearable device 710.

After the manufacturing portal patch program generator 715 receives the wearable device capabilities those capabilities are sent 750 to a manufacturer portal database 720. The manufacturing portal database 720 may then send standard condition criteria and condition duration information 760 to a manufacturing portal doctor/pharmacist GUI 725.

The manufacturing portal doctor/pharmacist GUI 725 may then optionally send modified condition criteria and condition duration information 770 to the manufacturer portal database 720 when a doctor wishes to change dosage levels. Next the manufacturing portal doctor/pharmacist GUI 725 approves a current set of condition criteria and condition duration settings 775, and those settings are updated in the manufacturing portal database. Next the approved condition criteria and condition duration information are sent 780 to the manufacturing portal patch program generator 715. The manufacturing portal patch program generator 715 then sends a patch program 785 to the wearable device 710. Finally the wearable device transmits a patch program to the patch 790.

Figure 8:
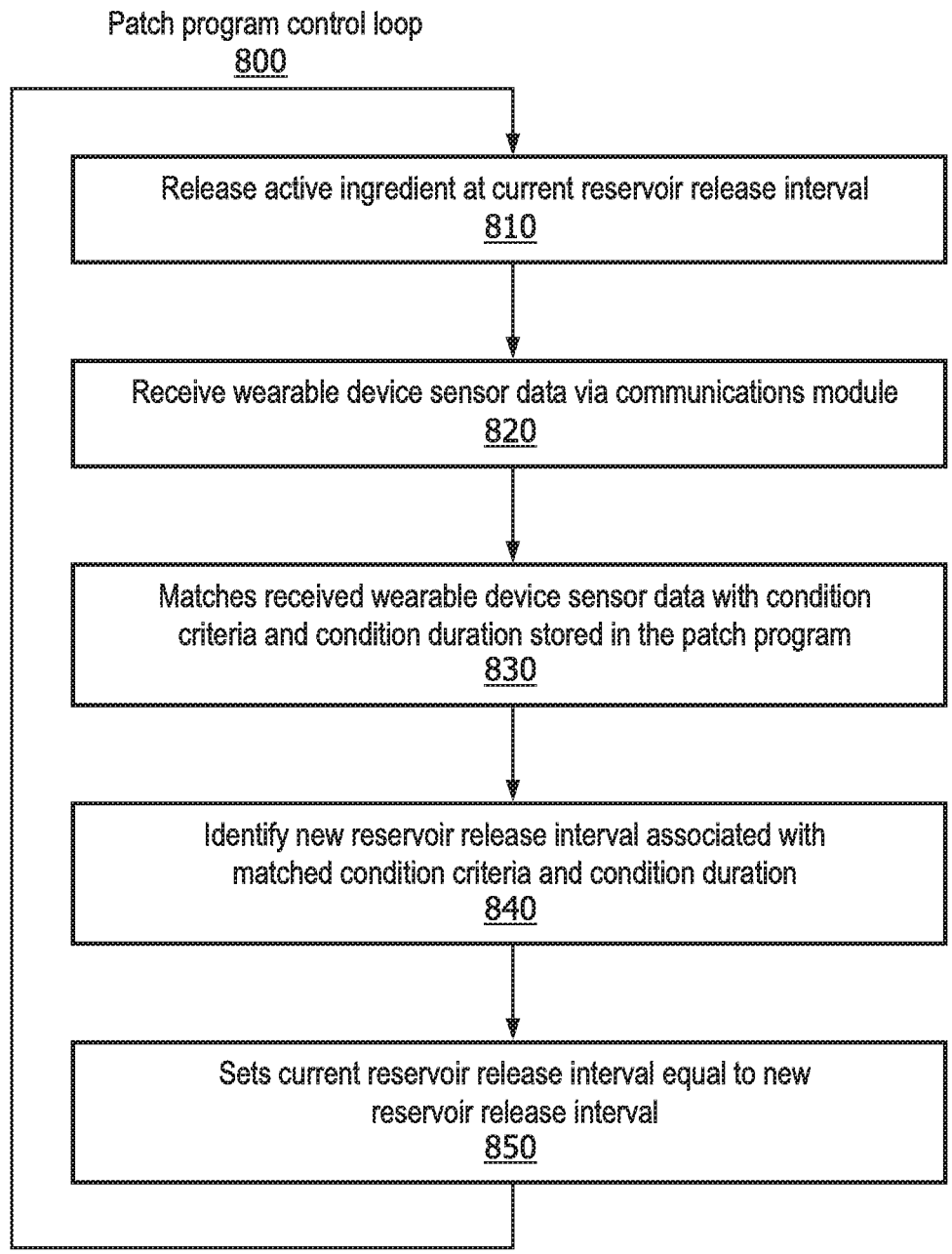
FIG. 8 illustrates an illustrative patch program loop flow chart according to an embodiment of the present invention.

FIG. 8 illustrates an illustrative patch program loop flow chart. A first step 810 in FIG. 8 releases an active ingredient at a current or initial release level. In second step 820 in the flow chart a wearable device receives sensor data over a communications module or interface. Next in a third step 830, wearable device sensor data received at the wearable device is matched with criteria, condition, and duration information stored by the patch program. In a fourth step 840 of the flow chart, a new reservoir release interval is determined using an algorithm. The algorithm may include input variables that correspond to a current criteria and a current sensed condition of a patient. Result information output from the algorithm may be used to change the current reservoir release level of an active ingredient in a smart patch in the last step 850 of FIG. 8.

The various methods may be performed by software operating in conjunction with hardware. For example, instructions executed by a processor, the instructions otherwise stored in a non-transitory computer readable medium such as memory. Various interfaces may be implemented—both communications and interface. One skilled in the art will appreciate the various requisite components of a mobile device and integration of the same with one or more of the foregoing figures and/or descriptions.

While various embodiments have been described above, it should be understood that they have been presented by way of example only, and not limitation. The descriptions are not intended to limit the scope of the invention to the particular forms set forth herein. Thus, the breadth and scope of a preferred embodiment should not be limited by any of the above-described exemplary embodiments. It should be understood that the above description is illustrative and not restrictive. To the contrary, the present descriptions are intended to cover such alternatives, modifications, and equivalents as may be included within the spirit and scope of the invention as defined by the appended claims and otherwise appreciated by one of ordinary skill in the art. The scope of the invention should, therefore, be determined not with reference to the above description, but instead should be determined with reference to the appended claims along with their full scope of equivalents.

The invention claimed is:

1. A computer-implemented method for dispensing a medication at a medication-dispensing patch, the method comprising:

receiving a transmission at a wearable device, wherein the transmission identifies the medication-dispensing patch;

transmitting information corresponding to the identified medication-dispensing patch from the wearable device to an external computing device;

receiving, by the wearable device from the external computing device, a dosage of a medication dispensed by the identified medication-dispensing patch;

transmitting the received dosage from the wearable device to the identified medication-dispensing patch; and modifying, with the wearable device, the dosage of the medication dispensed by the identified medication-dispensing patch based on analysis, by the wearable device, of physiological measurements made by the wearable device.

2. The method of claim 1, further comprising:
receiving sensor data from a sensor, the sensor data corresponding to a physiological measurement of a user of the wearable device; and
determining whether the sensor data corresponds to one or more criteria for administering the medication.

3. The method of claim 1, wherein the information received from the external computing device and the information transmitted from the wearable device include a time interval identifying how frequently the dosage of medication should be dispensed.

4. The method of claim 1, wherein the energy transmitted wirelessly from the wearable device to the identified medication-dispensing patch is configured for providing power to the identified medication-dispensing patch.

5. The method of claim 1, further comprising:
receiving sensor data sensed by a sensor at the identified medication-dispensing patch over a wireless communication interface at the wearable device;
receiving sensor data from a sensor at the wearable device;
comparing the sensor data received from the identified medication-dispensing patch and the sensor data sensed at the sensor at the wearable device with one or more criteria;
determining whether the dosage of medication dispensed by the identified medication-dispensing patch should be modified according to the one or more criteria; and
transmitting information from the wearable device to the identified medication-dispensing patch that modifies the dosage of medication dispensed by the identified medication-dispensing patch.

6. A non-transitory computer readable storage medium having embodied thereon a program executable by a processor to perform a method for dispensing a medication at a medication-dispensing patch, the non-transitory computer readable storage medium comprising:
instructions for receiving a transmission over a communications module at a wearable device, wherein the transmission is configured for identifying the medication-dispensing patch;
instructions for transmitting information corresponding to the identified medication-dispensing patch to an external computing device using the communications module;
instructions for receiving by the wearable device from the external computing device using the communications module, a dosage of a medication dispensed by the identified medication-dispensing patch; and
instructions for transmitting the received dosage from the wearable device to the identified medication-dispensing patch using the communications module; and
instructions for modifying, with the wearable device, the dosage of the medication dispensed by the identified medication-dispensing patch based on analysis, by the wearable device, of physiological measurements made by the wearable device.

7. The non-transitory computer readable storage medium of claim 6, further comprising:
instructions for analyzing sensor data sensed by a sensor, the sensor data corresponding to a physiological measurement of a user of the wearable device; and
instructions for determining whether the sensor data corresponds to one or more criteria for administering the medication.

8. The non-transitory computer readable storage medium of claim 6, wherein the information received from the external computer device and the information transmitted from the wearable device include a time interval identifying how frequently the dosage of medication should be dispensed.

9. The non-transitory computer readable storage medium of claim 6, further comprising:
instructions for dispensing the dosage of the medication after receiving the information transmitted from the wearable device.

10. The non-transitory computer readable storage medium of claim 6, further comprising:
instructions for transmitting energy wirelessly from the wearable device to the identified medication-dispensing patch and providing power to the identified medication-dispensing patch.

11. The non-transitory computer readable storage medium of claim 6, further comprising:
instructions for storing sensor data sensed by a sensor at the identified medication-dispensing patch, wherein the sensor data was received over a wireless communication interface at the wearable device;
instructions for storing sensor data from a sensor at the wearable device;
instructions for comparing the sensor data received from the identified medication-dispensing patch and the sensor data sensed at the sensor at the wearable device with one or more criteria; and
instructions for determining whether the dosage of medication dispensed by the identified medication-dispensing patch should be modified based on the one or more criteria; and
instructions for transmitting information from the wearable device to the identified medication-dispensing patch that modifies the dosage of medication dispensed by the identified medication-dispensing patch.

12. A system for dispensing a medication, the system comprising:
a medication-dispensing patch configured to communicate over a wireless communication network;
an external computing device configured to communicate over the wireless communication network; and
a wearable device configured to
receive a transmission that identifies the medication-dispensing patch,
transmit the received identification of the medication-dispensing patch to the external computing device,
receive from the external computing device, a dosage of a medication dispensed by the identified medication-dispensing patch,
transmit the received dosage from the wearable device to the identified medication-dispensing patch; and
modify, with the wearable device, the dosage of the medication dispensed by the identified medication-dispensing patch based on analysis, by the wearable device, of physiological measurements made by the wearable device.

13. The system of claim 12, wherein the wearable device comprises:
a sensor configured to sense sensor data corresponding to a physiological measurement of a user of the wearable device;
a processor configured to execute instructions stored in a memory to determine that the sensor data corresponds to one or more criteria for administering the medication; and
a communication module configured to transmit information based on the one or more criteria, wherein the information transmitted is configured for instructing the identified medication-dispensing patch to dispense the dosage, a modified dosage, or no dosage of the medication.

* * * * *